(12) United States Patent
Hueffer et al.

(10) Patent No.: US 7,410,504 B2
(45) Date of Patent: Aug. 12, 2008

(54) ADDUCTS BASED ON CYCLIC COMPOUNDS AND THE USE THEREOF AS TANNING AGENTS AND CURING AGENTS

(75) Inventors: Stephan Hueffer, Ludwigshafen (DE); Oliver Reese, Ludwigshafen am Rhein (DE); Walter Gramlich, Mannheim (DE); Stefan Schroeder, Neuleiningen (DE); Guenter Scherr, Ludwigshafen (DE); Volker Bach, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/543,495

(22) PCT Filed: Jan. 21, 2004

(86) PCT No.: PCT/EP2004/000454

§ 371 (c)(1),
(2), (4) Date: Jul. 27, 2005

(87) PCT Pub. No.: WO2004/067781

PCT Pub. Date: Aug. 12, 2004

(65) Prior Publication Data
US 2006/0101583 A1 May 18, 2006

(30) Foreign Application Priority Data
Jan. 28, 2003 (DE) ................. 103 03 311

(51) Int. Cl.
C14C 3/18 (2006.01)
C07D 309/30 (2006.01)

(52) U.S. Cl. ........................ 8/94.33; 568/483

(58) Field of Classification Search ................ 8/94.1 R, 8/94.33; 568/483
See application file for complete search history.

(56) References Cited

U.S. PATENT DOCUMENTS

| | | | | |
|---|---|---|---|---|
| 2,546,018 A | | 3/1951 | Smith et al. | |
| 2,624,764 A | * | 1/1953 | Emerson et al. | 568/322 |
| 2,941,859 A | * | 6/1960 | Fein et al. | 8/94.33 |
| 3,983,252 A | * | 9/1976 | Buchalter | 514/698 |
| 5,130,369 A | * | 7/1992 | Hughes et al. | 524/846 |
| 6,033,442 A | * | 3/2000 | Denzinger et al. | 8/94.33 |
| 2005/0125906 A1 | | 6/2005 | Hueffer et al. | |

FOREIGN PATENT DOCUMENTS

| | | |
|---|---|---|
| DE | 38 11 267 | 5/1989 |
| DE | 44 44 709 | 6/1996 |
| EP | 0 066 224 | 12/1982 |
| GB | 1 462 309 | 1/1977 |
| GB | 1462309 | * 1/1977 |
| WO | 03/095681 | 11/2003 |
| WO | 2004/067782 | 8/2004 |

OTHER PUBLICATIONS

Lepage, Lucette et al. "Synthese de dialdehydes-1,5 dieniques par reaction en milieu acide, d'aldehydes aromatiques avec le methoxy-2 dihydro-3,4 2H-pyranne", Bull. Soc. Chim. France, pp. 591-594, XP002285012, with English abstract 1988.
Heidemann, Eckhardt et al. "Leather". Ullmann's Encyclopedia of Industrial Chemistry, vol. A15, pp. 259-281 1988.
Herfeld, H. Bibliothek des Leders, vol. 2, p. 191, Umschau Verlag Frankfurt 1988.
Vauck/Mueller, Grundoperationen chemischer Verfahrenstechnik, VCH Weinheim, vol. 7, pp. 638-740 and 765-766 1988.
U.S. Appl. No. 10/543,495, filed Jul. 27, 2005, Hueffer, et al.
U.S. Appl. No. 10/543,605, filed Jul. 28, 2005, Hueffer, et al.

* cited by examiner

*Primary Examiner*—Lorna M. Douyon
*Assistant Examiner*—Amina Khan
(74) *Attorney, Agent, or Firm*—Oblon, Spivak, McClelland, Maier & Neustadt, P.C.

(57) ABSTRACT

Adducts are obtained by reacting carbonyl compounds of the formula I

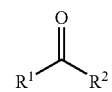

where $R^1$ and $R^2$ are as defined, with cyclic compounds of the formula II

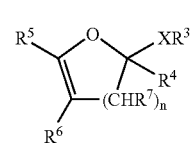

where X is selected from oxygen, sulfur and N—$R^8$, $R^3$-$R^8$ are as defined, and n is an integer from 1 to 4, which adducts are useful as tanning agents and preservatives.

29 Claims, No Drawings

ADDUCTS BASED ON CYCLIC COMPOUNDS AND THE USE THEREOF AS TANNING AGENTS AND CURING AGENTS

The present invention relates to adducts obtainable by reacting carbonyl compounds of the formula I

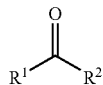

where
$R^1$ and $R^2$ are selected from hydrogen, $C_1$-$C_{12}$-alkyl, $C_3$-$C_{12}$-cycloalkyl, substituted or unsubstituted, $C_7$-$C_{13}$-aralkyl, $C_6$-$C_{14}$-aryl, substituted or unsubstituted, it being possible for $R^1$ and $R^2$ to be linked to one another with formation of a ring, with cyclic compounds of the formula II

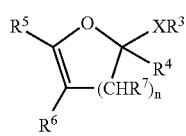

where
X is selected from oxygen, sulfur and N—$R^8$,
$R^3$ and $R^8$ are identical or different and are selected from hydrogen, $C_1$-$C_{12}$-alkyl, $C_3$-$C_{12}$-cycloalkyl, substituted or unsubstituted, $C_7$-$C_{13}$-aralkyl, $C_6$-$C_{14}$-aryl, substituted or unsubstituted, formyl, CO—$C_1$-$C_{12}$-alkyl, CO—$C_3$-$C_{12}$-cycloalkyl, substituted or unsubstituted, CO—$C_7$-$C_{13}$-aralkyl, CO—$C_6$-$C_{14}$-aryl, where X is N—$R^8$, it being possible for $R^3$ and $R^8$ to be linked to one another with formation of a ring;
$R^4$, $R^5$ and $R^6$ are identical or different and are selected from hydrogen, $C_1$-$C_{12}$-alkyl, $C_3$-$C_{12}$-cycloalkyl, substituted or unsubstituted, $C_7$-$C_{13}$-aralkyl, $C_6$-$C_{14}$-aryl, substituted or unsubstituted, it being possible in each case for two neighboring radicals to be linked to one another with formation of a ring;
n is an integer in the range from 1 to 4;
$R^7$ are identical or different and are selected from hydrogen, $C_1$-$C_{12}$-alkyl, $C_3$-$C_{12}$-cycloalkyl, substituted or unsubstituted, $C_7$-$C_{13}$-aralkyl, $C_6$-$C_{14}$-aryl, substituted and unsubstituted, it being possible for $R^7$ to be linked to $R^6$ or in each case two neighboring radicals $R^7$ to be linked to one another with formation of a ring.

Chrome tanning has been an important chemical treatment in leather production for more than 100 years, cf. for example *Ullmann's Encyclopedia of Industrial Chemistry*, Volume A15, pages 259 to 282 and in particular page 268 et seq., 5th edition (1990), Verlag Chemie Weinheim. For ecological reasons, however, alternatives to chrome tanning are being sought. In the conventional chrome tanning, chromium salts in an amount of from 1.5 to 8% by weight, based on the pelt weight of the leather, or even more are available. In general, a considerable part of this is not bound and enters the wastewater. Although it is possible to free the wastewater from considerable amounts of chromium by chemical treatment with, for example, lime and iron salts, chromium-containing sludges result and have to be disposed of on special landfills or worked up in an expensive procedure.

Moreover, for example, the splitting of the hides and the leveling of the leather gives rise to chromium-containing leather wastes which may account for from about 8 to 15% by weight, based on the hide weight, and likewise have to be disposed of in an expensive procedure.

There has been no lack of attempts to reduce the chromium pollution of the wastewaters, for example by recycling of the chrome tanning liquor or chromium recycling methods. However, these methods have as a whole been unsatisfactory and in particular are not capable of solving the problem of chromium-containing leather wastes.

Furthermore, processes in which some or all of the chromium was replaced by organic tanning agents are known. The use of the syntans, i.e. sulfonated condensates of formaldehyde and phenol or sulfonated naphthalene/formaldehyde condensates, may be mentioned. The use of vegetable tanning agents may furthermore be mentioned. However, both classes of tanning agents result in a high COD of the wastewater and are also unacceptable for environmental reasons. Moreover, it has been found that the lightfastness of the leather is often unsatisfactory when sulfonated phenol/formaldehyde condensates are used (*Ullmann's Encyclopedia of Industrial Chemistry*, Volume A15, pages 259 to 282 and in particular page 270 et seq., 5th edition (1990), Verlag Chemie Weinheim).

Tanning with the use of aldehydes, in particular dialdehydes, for example glutaraldehyde, is furthermore known, cf. for example H. Herfeld, Bibliothek des Leders, Volume III, page 191, Umschau Verlag Frankfurt/Main, 1984. However, a disadvantage is that, with small amounts of glutaraldehyde, for example from 0.5 to 0.9% by weight (based on the pelt weight), the shrinkage temperatures do not exceed 70° C. and the semifinished products used can therefore be dried only to an insufficient extent. During the shaving, gluing occurs on the flesh side of the leather and adversely affects the quality of the leather.

When larger amounts of glutaraldehyde are used, work safety problems may arise owing to the toxic properties of the glutaraldehyde. Moreover, it is observed that in general completely tanned leathers are obtained and that subsequent variable processing, as is desired in many tanneries, is no longer possible.

It is known that glutaraldehyde can be used in partially or completely acetalated form for tanning, for example as methylacetal (*Ullmann's Encyclopedia of Industrial Chemistry*, Volume A15, page 259 to 282 and in particular page 273 et seq., 5th edition (1990), Verlag Chemie Weinheim). However, the tanned semifinished products described generally rapidly tend to yellow.

DE-C 38 11 267 discloses that acetalation of glutaraldehyde or other dialdehydes which have 2 to 8 carbon atoms with short-chain alkylglycols, alkylpolyglycols, aliphatic alcohols, glycerol or saccharides has advantageous effects. However, the vapor pressure of dialdehydes, which readily reform from the very hydrolysis-sensitive acetals, is still marked. Furthermore, the performance characteristics of the leathers thus obtained can be further improved.

It is an object of the present invention to provide a novel process for the pretanning, tanning and posttanning of animal hides, which process avoids the abovementioned disadvantages. In particular, it is an object of the present invention to provide a tanning agent which avoids the disadvantages described above.

We have found that this object is achieved by the adducts defined at the outset. In formula I

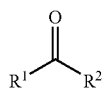

R¹ and R² are identical or different and are selected from
  hydrogen,
  $C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl and sec-hexyl, particularly preferably $C_1$-$C_4$-alkyl, such as methyl, ethyl, n-propyl, isopropyl, n-butyl, isobutyl, sec-butyl and tert-butyl, very particularly preferably methyl;
  $C_3$-$C_{12}$-cycloalkyl, such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;
    examples of substituted cycloalkyl radicals are: 2-methylcyclopentyl, 3-methylcyclopentyl, cis-2,4-dimethylcyclopentyl, trans-2,4-dimethylcyclopentyl 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-Chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethylcyclopentyl, 3-thiomethylcyclohexyl and further derivatives;
  $C_7$-$C_{13}$-aralkyl, preferably $C_7$— to $C_{12}$-phenylalkyl, such as benzyl, 1-phenethyl, 2-phenethyl, 1-phenypropyl, 2-phenylpropyl, 3-phenylpropyl, neophyl(1-methyl-1-phenyl-ethyl), 1-phenylbutyl, 2-phenylbutyl, 3-phenylbutyl and 4-phenylbutyl, particularly preferably benzyl,
  $C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl, unsubstituted or substituted by one or more
    $C_1$-$C_{12}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$-$C_4$-alkyl, such as methyl, ethyl, n-propyl, isopropyl, n-butyl, isobutyl, sec-butyl and tert-butyl;
    halogens, such as fluorine, chlorine, bromine and iodine, chlorine and bromine being preferred,
    $C_1$-$C_{12}$-alkoxy groups, preferably $C_1$-$C_6$-alkoxy groups, such as methoxy, ethoxy, n-propoxy, isopropoxy, n-butoxy, isobutoxy, sec-butoxy, tert-butoxy, n-pentyloxy, isopentyloxy, n-hexyloxy and isohexyloxy, particularly preferably methoxy, ethoxy, n-propoxy and n-butoxy.

In a particular embodiment, R¹ and R² are covalently bonded to one another with formation of a 4- to 13-membered ring. Thus, R¹ and R² together may be $C_3$-$C_8$-alkylene, unsubstituted or substituted by, for example, together $C_3$-$C_8$-alkylene, unsubstituted or substituted by, for example, $C_1$-$C_{12}$-alkyl or $C_6$-$C_{14}$-aryl. Examples are —(CH₂)₃—, —(CH₂)₂—CH(CH₃)—, —(CH₂)₂—CH(C₂H₅)—, —(CH₂)₂—CH(C₆H₅)—, —(CH₂)₄—, —(CH₂)₅—, —(CH₂)₆—, —(CH₂)₇—, —CH(CH₃)—CH₂—CH₂—CH(CH₃)—, —CH(CH₃)—CH₂—CH₂—CH₂—CH(CH₃)—, preferably $C_3$-$C_5$-allkylene, for example —(CH₂)₃—, —(CH₂)₄—, —(CH₂)₅—.

R¹ and R² are very particularly preferably each methyl.

In cyclic compounds of the formula II

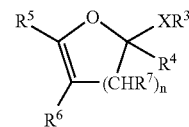

the variables are defined as follows.

X is selected from oxygen, sulfur and N—R⁸, oxygen being preferred.

R³ and R⁸ are identical or different and are selected from hydrogen,
  $C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$-$C_4$-alkyl, such as methyl, ethyl, n-propyl, isopropyl, n-butyl, isobutyl, sec-butyl and tert-butyl, very particularly preferably methyl;
  $C_3$-$C_{12}$-cycloalkyl, such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;
    examples of substituted cycloalkyl groups are: 2-methylcyclopentyl, 3-methylcyclopentyl, cis-2,4-dimethylcyclopentyl, trans-2,4-dimethylcyclopentyl, 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethylcyclopentyl, 3-thiomethylcyclohexyl;
  $C_7$-$C_{13}$-aralkyl, preferably $C_7$— to $C_{12}$-phenylalkyl, such as benzyl, 1-phenethyl, 2-phenethyl, 1-phenylpropyl, 2-phenylpropyl, 3-phenylpropyl, neophyl (1-methyl-1-phenyl-ethyl), 1-phenylbutyl, 2-phenylbutyl, 3-phenylbutyl and 4-phenylbutyl, particularly preferably benzyl, $C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl, unsubstituted or substituted $C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl, substituted by one or more $C_1$-$C_{12}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$-$C_4$-alkyl, such as methyl, ethyl, n-propyl, isopropyl, n-butyl, isobutyl, sec-butyl and tert-butyl;

halogens, such as fluorine, chlorine, bromine and iodine, chlorine and bromine being preferred, $C_1$-$C_{12}$-alkoxy groups, preferably $C_1$-$C_6$-alkoxy groups, such as methoxy, ethoxy, n-propoxy, isopropoxy, n-butoxy, isobutoxy, sec-butoxy, tert-butoxy, n-pentyloxy, isopentyloxy, n-hexyloxy and isohexyloxy, particularly preferably methoxy, ethoxy, n-propoxy and n-butoxy;

formyl,

CO—$C_1$-$C_{12}$-alkyl, such as acetyl, propionyl, n-butyryl, isobutyryl, sec-butyryl, tert-butyryl, n-valeroyl, isovaleroyl, sec-valeroyl, n-capryl and n-dodecanoyl; preferably CO—$C_1$-$C_4$-alkyl, such as acetyl, propionyl, n-butyryl, isobutyryl, sec-butyryl and tert-butyryl, very particularly preferably acetyl;

CO—$C_3$-$C_{12}$-cycloalkyl, such as cyclopropylcarbonyl, cyclobutylcarbonyl, cyclopentylcarbonyl, cyclohexylcarbonyl, cycloheptylcarbonyl, cyclooctylcarbonyl, cyclononylcarbonyl, cyclodecylcarbonyl, cycloundecylcarbonyl and cyclododecylcarbonyl; preferably cyclopentylcarbonyl, cyclohexylcarbonyl and cycloheptylcarbonyl;

examples of substituted cycloalkyl groups are: 2-methylcyclopentylcarbonyl, 3-methylcyclopentylcarbonyl, 2-methylcyclohexylcarbonyl, 3-methylcyclohexylcarbonyl, 4-methylcyclohexylcarbonyl, cis-2,5-dimethylcyclohexylcarbonyl, trans-2,5-dimethylcyclohexylcarbonyl, 2-methoxycyclopentylcarbonyl, 2-methoxycyclohexylcarbonyl, 3-methoxycyclopentylcarbonyl, 3-methoxycyclohexylcarbonyl, 2-chlorocyclopentylcarbonyl, 3-chlorocyclopentylcarbonyl, 2,4-dichlorocyclopentylcarbonyl, 2-chlorocyclohexylcarbonyl, 3-chlorocyclohexylcarbonyl, 4-chlorocyclohexylcarbonyl, 2,5-dichlorocyclohexylcarbonyl, 2-thiomethylcyclopentylcarbonyl, 2-thiomethylcyclohexylcarbonyl, 3-thiomethyl-cyclopentylcarbonyl, 3-thiomethylcyclohexyl;

CO—$C_7$-$C_{13}$-aralkyl, preferably CO—$C_7$-$C_{12}$-phenylalkyl, such as phenylacetyl and ω-phenylpropionyl, particularly preferably phenylacetyl;

$C_6$-$C_{14}$-aryl, for example benzoyl, 1-naphthoyl, 2-naphthoyl, 1-anthroyl, 2-anthroyl, 9-anthroyl, 1-phenanthroyl, 2-phenanthroyl, 3-phenanthroyl, 4-phenanthroyl and 9-phenanthroyl, preferably benzoyl, 1-naphthoyl and 2-naphthoyl, particularly preferably benzoyl.

$R^4$, $R^5$ and $R^6$ are identical or different and are selected from hydrogen, $C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$-$C_4$-alkyl, such as methyl, ethyl, n-propyl, isopropyl, n-butyl, isobutyl, sec-butyl and tert-butyl, very particularly preferably methyl;

$C_3$-$C_{12}$-cycloalkyl, substituted or unsubstituted, such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethyl-cyclopentyl, 3-thiomethylcyclohexyl;

$C_7$-$C_{13}$-aralkyl, preferably $C_7$— to $C_{12}$-phenylalkyl, such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl, $C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl, unsubstituted or substituted $C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl, unsubstituted or substituted by one or more $C_1$-$C_{12}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$-$C_4$-alkyl, such as methyl, ethyl, n-propyl, isopropyl, n-butyl, isobutyl, sec-butyl and tert-butyl;

halogens, such as fluorine, chlorine, bromine and iodine, chlorine and bromine being preferred, $C_1$-$C_{12}$-alkoxy groups, preferably $C_1$-$C_6$-alkoxy groups, such as methoxy, ethoxy, n-propoxy, isopropoxy, n-butoxy, isobutoxy, sec-butoxy, tert-butoxy, n-pentyloxy, isopentyloxy, n-hexyloxy and isohexyloxy, particularly preferably methoxy, ethoxy, n-propoxy and n-butoxy;

it being possible in each case for two neighboring radicals to be linked to one another with formation of a ring. For example, $R^4$ and $R^5$ together may be $C_1$-$C_8$-alkylene, unsubstituted or substituted by, for example, $C_1$-$C_{12}$-alkyl or $C_6$-$C_{14}$-aryl. Examples are: —$CH_2$—, —$CH(CH_3)$—, —$(CH_2)_2$—, —$CH_2$—$CH(CH_3)$—, —$CH_2$—$CH(C_2H_5)$—, —$(CH_2)_3$—, —$(CH_2)_2$—$CH(CH_3)$—, —$(CH_2)_2$—$CH(C_2H_5)$—, —$(CH_2)_2$—$CH(C_6H_5)$—, —$(CH_2)_4$—, —$(CH_2)_5$—, —$(CH_2)_6$—, —$(CH_2)_7$—, —$CH(CH_3)$—$CH_2$—$CH_2$—$CH(CH_3)$—, —$CH(CH_3)$—$CH_2$—$CH_2$—$CH_2$—$CH(CH_3)$—, preferably $C_3$-$C_5$-alkylene, for example —$(CH_2)_3$—, —$(CH_2)_4$—, —$(CH_2)_5$—.

n is an integer in the range from 1 to 4, in particular 2 or 3;

$R^7$ are identical or different and are selected from hydrogen, $C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl, and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, iso-hexyl, sec-hexyl, particularly preferably $C_1$-$C_4$-alkyl, such as methyl, ethyl, n-propyl, isopropyl, n-butyl, isobutyl, sec-butyl and tert-butyl, very particularly preferably methyl;

$C_3$-$C_{12}$-cycloalkyl, substituted or unsubstituted, such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

examples of substituted cycloalkyl groups are: 2-methylcyclopentyl, 3-methylcyclopentyl, cis-2,4-dimethylcyclopentyl, trans-2,4-dimethylcyclopentyl 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethylcyclopentyl, 3-thiomethylcyclohexyl;

$C_7$-$C_{13}$-aralkyl, preferably $C_7$- to $C_{12}$-phenylalkyl, such as benzyl, 1-phenethyl, 2-phenethyl, 1-phenylpropyl, 2-phenylpropyl, 3-phenylpropyl, neophyl(1-methyl-1-phenylethyl), 1-phenylbutyl, 2-phenylbutyl, 3-phenylbutyl and 4-phenylbutyl, particularly preferably benzyl, $C_6$-$C_{14}$-aryl, substituted or unsubstituted, substituted and unsubstituted $C_6$-$C_{14}$-aryl radicals being defined as above.

In one embodiment of the present invention, $R^7$ may be linked to $R^6$ or $R^7$ to $R^4$ or $R^7$ to $R^3$ or, where n is greater than 1, in each case two neighboring radicals $R^7$ may be linked to one another with formation of a ring. Thus, $R^6$ and $R^7$ together may be, for example, $C_1$-$C_8$-alkylene, unsubstituted or substituted by $C_1$-$C_{12}$-alkyl or $C_6$-$C_{14}$-aryl. Examples are: —$CH_2$—, —$CH(CH_3)$—, —$(CH_2)_2$—, —$CH_2$—$CH(CH_3)$—, —$CH_2$—$CH(C_2H_5)$—, —$(CH_2)_3$—, —$(CH_2)_2$—$CH(CH_3)$—, —$(CH_2)_2$—$CH(C_2H_5)$—, —$(CH_2)_2$—$CH(C_6H_5)$—, —$(CH_2)_4$—, —$(CH_2)_5$—, —$(CH_2)_6$—, —$(CH_2)_7$—, —$CH(CH_3)$—$CH_2$—$CH_2$—$CH(CH_3)$—, —$CH(CH_3)$—$CH_2$—$CH_2$—$CH_2$—$CH(CH_3)$—, preferably $C_3$-$C_5$-alkylene, for example —$(CH_2)_3$—, —$(CH_2)_4$—, —$(CH_2)_5$—.

$R^4$ $R^7$ are each very particularly preferably hydrogen. A very particularly preferably chosen compound of the formula IIIs 2-methoxy-2,3-dihydro-4H-pyran (formula II.1).

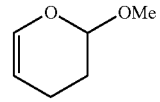

II.1

Very particularly preferred carbonyl compounds of the formula I are methyl ethyl ketone, formaldehyde and in particular acetone.

The novel adducts may be present in monomeric or dimeric form. The novel adducts can, however, also be present in oligomeric or polymeric form. Usually, the novel adducts are present as a mixture of dimers, oligomers or polymers, it furthermore being possible for the mixture to comprise compounds of the formula H—X—$R^3$ as a result of the preparation. Moreover, the novel adducts may be present as a mixture with impurities arising from the storage, for example dehydration products, oxidation products, hydrolysis products, crosslinked products or products of one or more retroaldol reactions.

The novel adducts can be prepared by reacting one or more carbonyl compounds of the formula I with one or more cyclic compounds of the formula II.

The present invention furthermore relates to a process for the preparation of the novel adducts. The novel process starts from at least one cyclic compound of the formula II and at least one carbonyl compound of the formula I, which are reacted with one another.

In one embodiment of the novel process, at least one cyclic compound of the formula II is reacted with up to 1 000, preferably up to 500, particularly preferably up to 200, mol % of at least one carbonyl compound of the formula I.

The novel process is preferably carried out at from 0 to 120° C., in particular from 20 to 85° C. The reaction can be carried out at any desired pressures from 0.1 to 100 bar, preferably at atmospheric pressure. The reaction is advantageously effected in the presence of a solvent, for example water, toluene, petroleum ether or n-heptane, but the addition of solvents is not necessary. Where the carbonyl compound of the formula I is liquid under reaction conditions, the use of solvents is not necessary for carrying out the novel process.

Some or all of the water formed during the reaction can be distilled off—together with H—X—$R^3$ formed in the course of the reaction.

In one embodiment of the present invention, the novel process is carried out at acidic pH, i.e. for example at a pH of from 0.5 to 6.8, preferably from 0.7 to 4. Preferably, one or more acidic catalysts are used for carrying out the novel process at acidic pH.

Suitable acidic catalysts are, for example, phosphoric acid, in particular orthophosphoric acid, formic acid, acetic acid, acidic silica gels, acidic alumina, dilute sulfuric acid and sulfonic acids, for example methanesulfonic acid or paratoluenesulfonic acid. If nonaqueous solvents are employed, the use of $P_2O_5$ or a molecular sieve is conceivable. From 0.1 to 20% by weight, based on carbonyl compound I, of catalyst may be used.

From 10 minutes to 24 hours, preferably from one to three hours, are expedient as a reaction time for the formation of the novel adducts.

After the reaction, it is possible to work up the reaction mixtures formed by the novel process. Thus, any solvents used can be removed completely or to a certain extent, for example by distillation, e.g. under reduced pressure. For example, any acidic catalysts used can be neutralized, for example with aqueous alkaline solution, such as sodium hydroxide solution or potassium hydroxide solution. It is also possible to separate off unconverted starting materials, e.g. excess carbonyl compound of the formula I. Particularly where the carbonyl compound of the formula I is readily volatile, for example acetone or methyl ethyl ketone, it is advantageous to separate off carbonyl compounds of the formula I by distillation.

In some cases, the formation of a multiphase mixture is observed when carrying out the novel process. In said cases, it is possible to remove the respective aqueous phase by, for example, decanting or other methods known per se.

When the novel process is carried out under the conditions described above, byproducts and secondary products are usually formed as a result of the preparation, for example by elimination of water (dehydration), incomplete reactions, oxidation or intramolecular crosslinking. During the storage of the novel adducts, byproducts arising from the storage may furthermore occur, for example by elimination of water (dehydration), oxidations or dimerization, oligomerization or polymerization and by crosslinking.

It is possible to purify and to isolate the novel adducts.

The present invention furthermore relates to mixtures of the novel adducts with the byproducts described above and arising from the preparation and/or arising from the storage.

The present invention furthermore relates to the use of the novel adducts or of the novel mixtures for the production of semifinished products and of leather.

In one embodiment of the present invention, the novel adducts or the novel mixtures are used in the pretanning, tanning or posttanning of animal hides.

The present invention furthermore relates to the use of the novel adducts and of the novel mixtures for the pretanning, tanning or posttanning of animal hides and a process for the pretanning, tanning or posttanning of animal hides using the novel adducts or the novel mixtures.

The novel process for the pretanning, tanning or posttanning of animal hides, also referred to below as novel tanning process, starts from hides of animals, for example cattle, pigs, goats or deer, which have been pretreated by conventional methods. It is not important for the novel tanning process whether the animals were killed, for example by slaughtering, or have died of natural causes. The conventional methods for the pretreatment include, for example, liming, deliming, bating and pickling and mechanical operations, for example for fleshing the hides.

The novel tanning process is usually carried out in the presence of water.

The novel tanning process is carried out, for example, by a procedure in which one or more novel adducts, if desired as a mixture with byproducts arising from the preparation and/or arising from the storage, are added in one portion or in a plurality of portions immediately before or during a tanning step. The novel tanning process is preferably carried out at a pH of from 2.5 to 4, it frequently being observed that the pH increases by about 0.3 to three units while the novel tanning process is being carried out. It is also possible to increase the pH by about 0.3 to three units by adding basifying agents.

The novel tanning process is carried out in general at from 10 to 45° C., preferably from 20 to 30° C. A duration of from 10 minutes to 12 hours has proven useful, preferably from one to 3 hours. The novel tanning process can be carried out in any desired vessel customary in the tannery, for example by tumbling in barrels or in rotatable drums having internals.

In one variant of the novel tanning process, the novel adducts or the novel mixtures are used together with one or more conventional tanning agents, for example with chrome tanning agents, mineral tanning agents, syntans, polymer tanning agents or vegetable tanning agents, as described, for example, in *Ullmann's Encyclopedia of Industrial Chemistry*, Volume A15, pages 259 to 282 and in particular page 268 et seq., 5th edition (1990), Verlag Chemie Weinheim. The weight ratio of novel adduct or novel mixture to conventional tanning agent or to the sum of the conventional tanning agents is expediently from 0.01:1 to 100:1, any impurities of the adducts which are present and arise from the preparation or arise from the storage being included. In an advantageous variant of the novel process, only a few ppm of the conventional tanning agents are added to the novel adducts. However, it is particularly advantageous completely to dispense with the admixture of conventional tanning agents.

In one variant of the novel tanning process, one or more adducts, if desired together with byproducts arising from the preparation and/or arising from the storage, are added in one portion or in a plurality of portions before or during the pretanning, in a particular variant as early as in the pickle.

In a further variant of the novel tanning process, one or more adducts or novel mixtures are added, if desired together with byproducts arising from the preparation and/or arising from the storage, in one portion or in a plurality of portions before or during a posttanning step. This variant is also referred to below as novel posttanning process. The novel posttanning process starts from pretanned hides. These are treated with the novel adducts.

The novel posttanning process can be carried out under otherwise conventional conditions. Expediently, one or more, for example from 2 to 6, action steps are chosen, and washing with water can be effected between the action steps. The temperature during the individual action steps is in each case from 5 to 60° C., preferably from 20 to 45° C. Expediently, further compositions usually used during the posttanning are employed, for example fatliquoring agents, leather dyes or emulsifiers.

A further aspect of the present invention relates to tanning agents comprising one or more novel adducts as active components.

A further aspect of the present invention relates to semifinished products and leathers produced by the novel process. The novel leathers have an advantageous quality overall, for example smooth grains, more homogeneous tanning over the cross section, improved tensile strength and body and little tendency to discolor, in particular to yellow.

In a special embodiment of the novel tanning process, the novel adducts are used, if desired as mixtures with byproducts arising from the preparation or arising from the storage, in the form of active ingredients in powder form. The novel process furthermore relates to active ingredients in the form of powder, comprising from 10 to 100, preferably from 40 to 90%, by weight of one or more novel adducts, if desired as a mixture with byproducts arising from the preparation or arising from the storage, and from 0 to 90, preferably from 10 to 60%, by weight of one or more additives.

Suitable additives are as a rule solid particulate substances. They are preferably chosen from starch, silica, for example in the form of silica gel, in particular in the form of spheroidal silica gels, sheet silicates, alumina and mixed oxides of silicon and aluminum.

The novel active ingredients in the form of powder may consist of fine particles having a mean particle diameter of from 100 nm to 0.1 mm. The particle diameters follow a particle diameter distribution which can be narrow or broad. Bimodal particle size distributions are also conceivable. The particles themselves may be irregular or of spherical shape, spherical particle shapes being preferred. The novel active ingredients in the form of powder can be metered in the novel tanning process under particularly hygienic conditions.

The present invention furthermore relates to a process for the preparation of the novel active ingredients in the form of a powder. The novel process starts from novel adducts which are present in solution, suspension or emulsion or in isolated form and which may comprise byproducts arising from the preparation or arising from the storage. Particularly preferably, reaction solutions as obtained in the novel process in the case of the preparation of the novel adducts are used as starting materials.

It has proven useful initially to concentrate the reaction solutions to a residual solvent content of 50% by weight or less.

If desired, one or more additives are furthermore introduced.

The remaining volatile components are then removed. The resulting liquid, solid or oily concentrated reaction solutions are preferably sprayed in a spray dryer, preferably in a spray tower. Spray dryers are known to a person skilled in the art and are described, for example, in Vauck/Müller, *Grundoperationen chemischer Verfahrenstechnik*, VCH Weinheim, 1988, 7th edition, pages 638-740 and pages 765-766, and in the literature cited therein.

In a special embodiment of the novel tanning process, the novel adducts, if desired as mixtures with byproducts arising from the preparation or arising from the storage, are used in the form of suspensions, for example as aqueous suspensions.

In one embodiment of the novel tanning process, one or more novel adducts, if desired as mixtures with byproducts arising from the preparation or arising from the storage, are used in a form diluted with polar solvents. For example, alcohols or aqueous alcohols are suitable. Examples of suitable alcohols are ethylene glycol, glycerol, diethylene glycol, triethylene glycol and polyethylene glycol and mixtures of the above alcohols. Suitable concentrations of the polar solvent or solvents are, for example, from 1 to 80% by weight. In a special embodiment of the novel tanning process, one or more novel adducts, if desired as mixtures with byproducts arising from the preparation or arising from the storage, are used in a form diluted with polar solvents, and furthermore additives are admixed. Suitable additives are, for example, starch, silica, sheet silicates, alumina and mixed oxides of silicon and aluminum.

The present invention furthermore relates to mixtures of the novel adducts, if desired as mixtures with byproducts arising from the preparation or arising from the storage, with polar solvents, for example alcohols or aqueous alcohols.

A further aspect of the present invention relates to the use of the novel adducts, if desired as mixtures with byproducts arising from the preparation or arising from the storage, for preservation, and preservatives comprising the novel adducts or the novel mixtures. The novel preservatives are suitable for preserving products, for example cosmetic products, and surfaces.

The invention is explained by the Examples.

1. PREPARATION OF THE NOVEL ADDUCTS 1.1 TO 1.5

The molecular weight determinations were effected by gel permeation chromatography under the following conditions:

Stationary phase: hydroxyethyl methacrylate gel crosslinked with ethylene glycol dimethacrylate, commercially available as: HEMA BIO from PSS, Mainz, Germany, flow rate: 1.5 ml/min, concentration: 1% by weight in the mobile phase with internal standard, mobile phase: THF 30% by weight, acetonitrile 10% by weight, 0.1 molar aqueous $NaNO_3$ solution 60% by weight, internal standard: 0.01% by weight of benzophenone; detection: UV/vis at 254 nm.

1.1. Preparation of Adduct 1.1

In a 1 liter three-necked flask having a condenser, stirrer and thermometer, 114 g of 2-methoxy-2,3-dihydro-4H-pyran (formula II.1; 1 mol), 114 ml of water and 58 g of acetone (1 mol) and 24.6 g of an 85% by weight aqueous orthophosphoric acid were mixed and were refluxed for 3 hours. The pH was 1.

311 g of an aqueous dispersion of adduct 1.1 were obtained in the form of a honey-colored product having a broad molar mass distribution (Q=4.7) and an $M_n$ of 380 g.

1.2. Preparation of Adduct 1.2

In a 1 liter three-necked flask having a condenser, stirrer and thermometer, 128 g of 2-methoxy-2,3-dihydro-4H-pyran (formula II.1; 1,12 mol), 128 ml of water and 112 g of acetone (2 mol) were mixed with 21 g of a 50% by weight sulfuric acid and were refluxed for 3 hours. The pH was 0.9.

Thereafter, the condenser was replaced by a distillation bridge and aqueous acetone was distilled off over a period of 3 hours at 70-80° C. and 1 bar. The mixture was allowed to cool to room temperature and a pH of 5.2 was established with 25% by weight of aqueous sodium hydroxide solution. Thereafter, the mixture was transferred to a separating funnel and about 25 ml of an aqueous phase were separated off and discarded. 317 g of adduct 1.2 were obtained in the form of an amber-colored oily product having a broad molar mass distribution (Q=5.1) and an $M_n$ of 610 g.

1.3. Preparation of Adduct 1.3

In a 1 liter three-necked flask having a condenser, stirrer and thermometer, 141 g of 2-methoxy-2,3-dihydro-4H-pyran (formula II.1; 1.24 mol), 141 ml of water and 83.7 g of acetone (1.44 mol) were mixed with 11 g of 50% by weight of sulfuric acid and were refluxed for 3 hours. The pH was 0.9.

Thereafter, the condenser was replaced by a distillation bridge and aqueous acetone was distilled off over a period of 3 hours at 70-80° C. and 1 bar.

The mixture was allowed to cool to room temperature and a pH of 5.2 was established with 25% by weight of aqueous sodium hydroxide solution. Further volatile components were then distilled off at 55° C. and 450 mbar. 297 g of adduct 1.3 were obtained in the form of an amber-colored oily product having a broad molar mass distribution (Q=5.2) with an $M_n$ of 810 g.

1.4. Preparation of Adduct 1.4

In a 1 liter three-necked flask having a condenser, stirrer and thermometer, 141 g of 2-methoxy-2,3-dihydro-4H-pyran (formula II.1; 1.24 mol), 141 ml of water and 83.7 g of acetone (1.44 mol) were mixed with 70% by weight of methanesulfonic acid and were refluxed for 3 hours. The pH was 0.9.

Thereafter, the condenser was replaced by a distillation bridge and aqueous acetone was distilled off at 82° C. and atmospheric pressure volatile components over a period of 3 hours.

The mixture was allowed to cool to room temperature and a pH of 5.3 was established with 6 ml of 50% by weight aqueous sodium hydroxide solution. Further volatile components were then distilled off at 55° C. and 550 mbar over a period of one hour. 280 g of adduct 1.4 were obtained in the form of a yellow oily liquid having a broad molar mass distribution (Q=3.8) with an $M_n$ of 840 g.

1.5. Preparation of Adduct 1.5

In a 1 liter three-necked flask having a condenser, stirrer and thermometer, 141 g of 2-methoxy-2,3-dihydro-4H-pyran (formula II.1; 1.24 mol), 144.3 g of aqueous formalin solution (1.44 mol of formaldehyde) and 45 ml of water were mixed with 7.5 g of a 70% by weight methanesulfonic acid and were refluxed for 3 hours. The pH was 0.9. The condenser was then replaced by a distillation bridge and aqueous acetone was distilled off at 75° C. and atmospheric pressure over a period of 3 hours.

The mixture was allowed to cool to room temperature and a pH of 4.2 was established with about 9 ml of 50% by weight aqueous sodium hydroxide solution. Further volatile components were then distilled off at 49° C. and 35 mbar. 151 g of adduct 1.5 were obtained in the form of an oily brown product having a broad molar mass distribution (Q=4.6) with an $M_n$ of 1 120 g.

2. TANNING EXPERIMENTS

2.1. Inventive Tanning Experiment 2.1

Data in % by weight are based on the pickle weight unless stated otherwise. 750 ml of water and 3% by weight, based on the pickled pelt, of the adduct 1.1 were added to strips of pickled cattle pelt having a split thickness of 2.5 mm and each weighing 2 500 g at a pH of 3.0-3.2 and 25° C. in a 10 l barrel. After a drumming time of 60 minutes, 2% by weight of the sulfone tanning agent Basyntan® SW (BASF Aktiengesellschaft) were added and drumming was effected for a further 2 hours. The pH was then brought to 4.9-5.1 with 0.5% by weight of magnesium oxide in the course of 6 hours. The liquor was discharged and the hide was washed with 300 ml of water. After samming, the hides were shaved to 1.6-1.8 mm. The inventive semifinished product 2.1 was obtained.

The shavability was determined by experiments on a shaving machine. Shaving machines operate with rotating blades. In the case of poor shavability, the blades slid over the surface and the temperature on the surface of the leather increased so that horny fusion irreversibly damaged the hide. The rating was effected according to a rating system from 1 (very good) to 5 (poor).

2.2 to 2.5. Inventive Tanning Experiments 2.2 to 2.5 and Comparative Experiment C 2.6

The tanning experiment described above was repeated except that the inventive adduct 1.1 was replaced by the inventive adducts 1.2, 1.3, 1.4 and 1.5 respectively.

This correspondingly produced the inventive semifinished products 2.2, 2.3, 2.4 and 2.5 respectively.

Comparative experiment C 2.6 was carried out analogously, but the inventive adduct was replaced by 3% by weight of glutaraldehyde (50% by weight aqueous solution). The comparative semifinished product C 2.6 was obtained.

The shrinkage temperatures were determined according to the method from DIN 53 336 (year 1977), the method having been modified as follows:

Point 4.1: The samples have the dimensions 3 cm·1 cm; the thickness was not determined.

Point 4.2: Only one specimen per leather sample was tested instead of 2.

Point 6: Omitted

Point 7: The drying in the vacuum desiccator was omitted.

Point 8: The shrinkage temperature was measured when the pointer returned.

The rating of the shavability and of the yellowing were effected on the following rating scale: 1 very good, 2 good, 3 satisfactory, 4 adequate.

TABLE 1

Result of the tanning and analytical evaluation of inventive semifinished products

| Number | Semifinished product | Shavability | Shrinkage temperature [° C.] | Yellowing |
|---|---|---|---|---|
| 2.1 | 2.1 | 3 | 74.5 | 2 |
| 2.2 | 2.2 | 2.5 | 76 | 2.5 |
| 2.3 | 2.3 | 2 | 77.5 | 2.5 |
| 2.4 | 2.4 | 2 | 79 | 2 |
| 2.5 | 2.5 | 3 | 74 | 3.5 |
| C 2.6 | Glutaraldehyde | 3 | 77 | 4 |

3. PRODUCTION OF INVENTIVE LEATHERS AND COMPARATIVE EXPERIMENT

Data in % by weight are based on the shaved weight, unless stated otherwise.

3.1. Production of Leather 3.1 from Semifinished Product 2.1

1 800 g of semifinished product 2.1 was drummed together with the following agents for 20 minutes:

120% by weight of water, 5% by weight of the sulfone tanning agent Basyntan® SW (BASF Aktiengesellschaft) and 4% of a 30% by weight aqueous solution of a methacrylic acid homopolymer partially neutralized with NaOH and having the following analytical data: $M_n$ about 10 000; Fikentscher K value: 12 (determined as 1% by weight aqueous solution), viscosity of the 30% by weight solution: 65 mPa·s (DIN EN ISO 3219, 23° C.), pH 5.1.

6% by weight of the vegetable tanning agent Tara® (BASF Aktiengesellschaft) and 2% by weight of the resin tanning agent Relugan® S (BASF Aktiengesellschaft) and 2% by weight of the dye Luganil® brown NGB were then metered and the mixture was drummed. After two hours, a pH of 3.6 was established with formic acid. 6% by weight of Lipodermliquer CMG® (BASF Aktiengesellschaft) and 1% by weight of Lipamin OK® (BASF Aktiengesellschaft) were added as a fatliquoring component. After a drumming time of a further 60 minutes, the pH of 3.2 was established with formic acid. Before the liquor was discharged, a sample of the liquor was taken. The liquor was discharged.

The leather thus obtained was washed twice with 100% by weight of water each time, stored moist overnight, partly dried on a toggle frame at 50° C. and then dried. Leather 3.1 was obtained. After staking, leather 3.1 was assessed as below.

The evaluation was effected according to a rating system from 1 (very good) to 5 (poor). The evaluation of the liquor exhaustion was effected visually according to the criteria of residual dye (extinction) and turbidity (fatliquoring agent), from which the mean value was calculated.

Examples 3.2 to 3.5, Comparative Example C 3.6

The above example was repeated, but in each case with inventive semifinished product 2.2 to 2.5. For comparative example C 3.6, the semifinished product from comparative example C 2.6 was further processed. The evaluation of the performance characteristics is shown in table 2.

TABLE 2

| Leather | Liquor exhaustion | Body | Grain tightness | Softness | Tensile strength [N] | Stitch tear resistance | Levelness |
|---|---|---|---|---|---|---|---|
| 3.1 | 3 | 2.5 | 3 | 3.5 | 256 | 196 | 2.5 |
| 3.2 | 2.5 | 2.5 | 2 | 3 | 270 | 194 | 2.5 |
| 3.3 | 2 | 1.5 | 2.5 | 2 | 283 | 201 | 1 |
| 3.4 | 1.5 | 1 | 1.5 | 2 | 287 | 229 | 1 |
| 3.5 | 1.5 | 2.5 | 2 | 2.5 | 260 | 218 | 1.5 |
| C 3.6 | 3 | 3.5 | 3.5 | 3 | 247 | 191 | 3 |

The tensile strength was determined according to DIN 53328.

The stitch tear resistance was determined according to DIN 53331.

We claim:

1. An adduct obtained by reacting, in the presence of water and at an acid pH, at least one carbonyl compound of the formula I

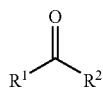

where
R$^1$ and R$^2$ are selected from hydrogen, C$_1$-C$_{12}$-alkyl, C$_3$-C$_{12}$-cycloalkyl, substituted or unsubstituted, C$_7$-C$_{13}$-aralkyl, C$_6$-C$_{14}$-aryl, substituted or unsubstituted, it being possible for R$^1$ and R$^2$ to be linked to one another with formation of a ring,
with at least one cyclic compound of the formula II

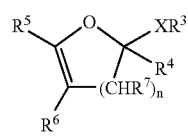

where
X is selected from the group consisting of oxygen, sulfur and N—R$^8$,
R$^3$ and R$^8$ are identical or different and are selected from hydrogen, C$_1$-C$_{12}$-alkyl, C$_3$-C$_{12}$-cycloalkyl, substituted or unsubstituted, C$_7$-C$_{13}$-aralkyl, C$_6$-C$_{14}$-aryl, substituted or unsubstituted, formyl, CO—C$_1$-C$_{12}$-alkyl, CO—C$_3$-C$_{12}$-cycloalkyl, substituted or unsubstituted, CO—C$_7$-C$_{13}$-aralkyl, CO—C$_6$-C$_{14}$-aryl, where X is N—R$^8$, it being possible for R$^3$ and R$^8$ to be linked to one another with formation of a ring;
R$^4$ and R$^5$ are each hydrogen, and R$^6$ is selected from the group consisting of hydrogen, C$_1$-C$_{12}$-alkyl, C$_3$-C$_{12}$-cycloalkyl, substituted or unsubstituted, C$_7$-C$_{13}$-aralkyl, C$_6$-C$_{14}$-aryl, substituted or unsubstituted, it being possible in each case for two neighboring radicals to be linked to one another with formation of a ring;
n is an integer in the range from 1 to 4;
R$^7$ identical or different and are selected from hydrogen, C$_1$-C$_{12}$-alkyl, C$_3$-C$_{12}$-cycloalkyl, substituted or unsubstituted, C$_7$-C$_{13}$-aralkyl, C$_6$-C$_{14}$-aryl, substituted or unsubstituted, it being possible for R$^7$ to be linked to R$^6$ or in each case two neighboring radicals R$^7$ to be linked to one another with formation of a ring.

2. The adduct as claimed in claim 1, wherein X is oxygen.

3. The adduct as claimed in claim 1, wherein R$^6$ to R$^7$ are each hydrogen.

4. A mixture comprising at least one adduct as claimed in claim 1 with byproducts arising from the preparation or storage thereof.

5. A process for the preparation of an adduct as claimed in claim 1 comprising reacting, in the presence of water and at an acid pH, at least one carbonyl compound of the formula I with at least one cyclic compound of the formula II.

6. A process for the production of semifinished products or leather, wherein an adduct as claimed in claim 1 is used.

7. The process as claimed in claim 6, wherein the adduct is used in a form diluted with a polar solvent.

8. The process as claimed in claim 7, wherein the adduct is used as an active ingredient in powder form.

9. An active ingredient in powder form, comprising from 10 to 100% by weight of the adduct as claimed in claim 1 and from 0 to 90% by weight of one or more additives.

10. The active ingredient in powder form as claimed in claim 9, in which the one or more additives are present, and are selected from the group consisting of starch, silica, sheet silicates, alumina and mixed oxides of silicon and aluminum.

11. A process for the preparation of an active ingredient in powder form as claimed in claim 9, wherein said active ingredient is obtained by spray-drying.

12. A process as claimed in claim 6, wherein the adduct is used in a form diluted with a polar solvent, in the presence of additives.

13. A process comprising preserving a product by incorporating the adduct as claimed in claim 1 in said product.

14. A process comprising preserving a product by incorporating the active ingredient in powder form as claimed in claim 9 in said product.

15. A process for the preparation of a mixture as claimed in claim 4, comprising reacting, in the presence of water and at an acid pH, at least one carbonyl compound of the formula I with at least one cyclic compound of the formula II.

16. A process for the production of semifinished products or leather, wherein a mixture as claimed in claim 4 is used.

17. The process as claimed in claim 16, wherein the mixture is used in a form diluted with a polar solvent.

18. The process as claimed in claim 17, wherein the mixture is used as an active ingredient in powder form.

19. An active ingredient in powder form, comprising from 10 to 100% by weight of a mixture as claimed in claim 4 and from 0 to 90% by weight of one or more additives.

20. The active ingredient in powder form as claimed in claim 19, in which the one or more additives are present, and are selected from the group consisting of starch, silica, sheet silicates, alumina and mixed oxides of silicon and aluminum.

21. A process for the preparation of an active ingredient in powder form as claimed in claim 19, wherein said active ingredient is obtained by spray-drying.

22. A process as claimed in claim 16, wherein the mixture is used in a form diluted with a polar solvent, in the presence of additives.

23. A process comprising preserving a product by incorporating the mixture as claimed in claim 4 in said product.

24. A process comprising preserving a product by incorporating the active ingredient in powder form as claimed in claim 19 in said product.

25. The adduct as claimed in claim 1, wherein the carbonyl compound comprises acetone and the cyclic compound comprises 2-methoxy-2,3-dihydro-4H-pyran.

26. The mixture as claimed in claim 4, wherein the carbonyl compound comprises acetone and the cyclic compound comprises 2-methoxy-2,3-dihydro-4H-pyran.

27. The adduct as claimed in claim 1, wherein the at least one carbonyl compound and the at least one cyclic compound are the only reactants, other than water and an acid.

28. The mixture as claimed in claim 4, wherein the at least one carbonyl compound and the at least one cyclic compound are the only reactants, other than water and an acid.

29. An adduct obtained by reacting, in the presence of water and at an acid pH, at least one carbonyl compound of the formula I

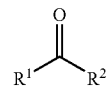

where $R^1$ and $R^2$ are selected from hydrogen, $C_1$-$C_{12}$-alkyl, $C_3$-$C_{12}$-cycloalkyl, substituted or unsubstituted, $C_7$-$C_{13}$-aralkyl, $C_6$-$C_{14}$-aryl, substituted or unsubstituted, it being possible for $R^1$ and $R^2$ to be linked to one another with formation of a ring, with at least one cyclic compound of the formula II

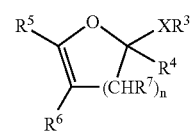

where

X is selected from the group consisting of oxygen, sulfur and N—$R^8$, $R^3$ and $R^8$ are identical or different and are selected from hydrogen, $C_1$-$C_{12}$-alkyl, $C_3$-$C_{12}$-cycloalkyl, substituted or unsubstituted, $C_7$-$C_{13}$-aralkyl, $C_6$-$C_{14}$-aryl, substituted or unsubstituted, formyl, CO—$C_1$-$C_{12}$-alkyl, CO—$C_3$-$C_{12}$-cycloalkyl, substituted or unsubstituted, CO—$C_7$-$C_{13}$-aralkyl, CO—$C_6$-$C_{14}$-aryl, where X is N—$R^8$, it being possible for $R^3$ and $R^8$ to be linked to one another with formation of a ring;

$R^4$ to $R^7$ are methyl;

and n is an integer in the range from 1 to 4.

* * * * *